(12) United States Patent
O'Brien et al.

(10) Patent No.: US 6,277,581 B1
(45) Date of Patent: Aug. 21, 2001

(54) ODC ALLELIC ANALYSIS METHOD FOR ASSESSING CARCINOGENIC SUSCEPTIBILITY

(75) Inventors: Thomas G. O'Brien; Yong Jun Guo, both of Drexel Hill, PA (US)

(73) Assignee: Lankenau Medical Research Center, Wynnewood, PA (US)

( * ) Notice: Subject to any disclaimer, the term of this patent is extended or adjusted under 35 U.S.C. 154(b) by 0 days.

(21) Appl. No.: 09/516,357

(22) Filed: Mar. 1, 2000

Related U.S. Application Data (60) Provisional application No. 60/122,309, filed on Mar. 1, 1999.

(51) Int. Cl.$^7$ .............................. C12Q 1/68; C12P 19/34; C12N 15/11; C07H 21/04
(52) U.S. Cl. .......................... 435/6; 435/91.2; 536/23.1; 536/24.3; 536/24.31; 536/24.33
(58) Field of Search ................... 435/6, 91.2; 536/23.1, 536/24.31, 24.33, 24.3

(56) References Cited

PUBLICATIONS

Fitzgerald et al. DNA, 1989 8(9): 623–634, GenEmbl, locus HUMSODA, Jan. 13, 1995.*
Auvinen et al., 1992, Nature 360:355–358.
Bello–Fernandez et al., 1993, Proc. Natl. Acad. Sci. USA 90:7804–7808.
Blackwood et al., 1992, Genes Dev. 6:71–80.
Clifford et al., 1995, Cancer Res. 55:1680–1686.
Gan et al., 1993, J. Histochem. Cytochem. 41:1185–1196.
Hibshoosh et al., 1991, Oncogene 6:739–743.
Hickok et al., 1987, DNA 6:179–187.
Klein et al., 1985 Immunol. Today 6:208–215.
Kostrikis et al., 1998, Science 279:1228–1229.
Luk et al., 1984, N. Engl. J. Med. 311:80–83.
Mimori et al., 1997, Dis. Colon Rectum 40:1095–1100.
Mori et al., 1996, Cancer 77[Suppl.]:1634;1638.
Moshier et al., 1993, Cancer Res. 53:2618–2622.
O'Brien et al, 1997, Cancer Res. 57:2630–2637.
Payne et al., 1982, Nature 295:209–214.
Schwab et al., 1984, Proc. Natl. Acad. Sci. USA 81:4940–4944.
Soler et al., 1998, Cancer Res. 58:1654–1659.
Solomon et al., 1993, Nucleic Acids Research 21:5372–5376.
Tobias et al., 1995, Oncogene 11:1721–1727.
Wagner et al., 1993, Cell Growth Diff. 4:789–883.
Walhout et al., 1998, Biochim. Biophys. Acta 1397:189–201.

* cited by examiner

Primary Examiner—W. Gary Jones
Assistant Examiner—B. J. Forman
(74) Attorney, Agent, or Firm—Akin, Gump, Strauss, Hauer & Feld, L.L.P.

(57) ABSTRACT

The invention includes kits and methods for assessing the susceptibility of a mammal such as a human for carcinogenesis. The methods comprise determining whether the mammal comprises a certain allele of the mammal's odc gene. The methods include use of a probe which binds specifically with a portion of one allele of the odc gene and which comprises a fluorescent label and a fluorescence quencher. The methods also include use of such a probe and a polymerase enzyme for amplifying a portion of the odc gene, the polymerase having exonuclease activity whereby the probe can be nucleolytically degraded.

29 Claims, 2 Drawing Sheets

Fig. 1

POLYMERIZATION

STRAND DISPLACEMENT

CLEAVAGE

POLYMERIZATION COMPLETED

+282 GGGCCCCGGG CACGTGTGCG GCGGCGCCTCG CCGGCCTGCA* GAGACACGTG GTCGCCGAG +340

Fig. 2A

+282 GGGCCCCGGG CACGTGTGCG GCGGCGCCTCG CCGGCCTGCG* GAGACACGTG GTCGCCGAG +340

Fig. 2B

ODC ALLELIC ANALYSIS METHOD FOR ASSESSING CARCINOGENIC SUSCEPTIBILITY

CROSS-REFERENCE TO RELATED APPLICATIONS

This application is entitled to priority pursuant to 35 U.S.C. §119(e) to U.S. provisional patent application No. 60/122,309, which was filed on Mar. 1, 1999.

BACKGROUND OF THE INVENTION

The invention relates, in a general sense, to assessing the susceptibility of mammals to carcinogenesis.

An individual's susceptibility to cancer is governed by the individual's genome and carcinogenic stimuli which the individual encounters in the environment. Although the carcinogenic potentials of many compounds and other stimuli (e.g. ionizing radiation) have been determined, assessing the importance of limiting exposure to such compounds is complicated by the fact that not all individuals are equally susceptible to the carcinogenic effects of the compounds. Thus, the genetic component of carcinogenic susceptibility limits accurate prediction of cancer rates among individuals, even in defined environments.

Prior art observations suggest that up-regulation of the mammalian gene (odc) encoding ornithine decarboxylase is associated with enhanced susceptibility to carcinogenesis (Luk et al., 1984, N. Engl. J. Med. 311:80–83). Other prior art references indicate that overexpression of the odc gene increases susceptibility of mammalian cells for the tumor promotion stage of carcinogenesis, but that over-expression of odc is not, by itself, a sufficient condition for carcinogenesis (Clifford et al., 1995, Cancer Res. 55:1680–1686; Auvinen et al., 1992, Nature 360:355–358; Moshier et al., 1993, Cancer Res. 53:2618–2622; Hibshoosh et al., 1991, Oncogene 6:739–743; O'Brien et al, 1997, Cancer Res. 57:2630–2637).

It is known that there are at least two alleles of the human odc gene, which have been observed as different PstI restriction fragment length polymorphisms (RFLP; Hickok et al., 1987, DNA 6:179–187).

It is believed that the odc gene product, ornithine decarboxylase, is involved in establishing cellular polyamine levels, and that the susceptibility of a tissue to carcinogenesis is related to polyamine levels in the cells of the tissue. Transcription of the odc gene is activated by the protein designated Myc (Bello-Fernandez et al., 1993, Proc. Natl. Acad. Sci. USA 90:7804–7808; Tobias et al., 1995, Oncogene 11:1721–1727; Wagner et al., 1993, Cell Growth Diff. 4:789–883). Such regulation is effected by binding of Myc/Max heterodimers to one or more of the three Myc binding elements (also called "E-boxes") in the human odc gene. These E-boxes are located at nucleotide residues −485 to −480 (relative to the transcription start site) in the odc 5'-promoter region and at nucleotide residues +292 to +297 and +326 to +331 in the first intron of the odc gene. The fact that the E-box located in the promoter region of the human gene is not conserved in the rat and mouse genes, suggests that the other two E-boxes are the physiologically important regulatory elements.

In normal cells, expression of c-myc (the gene encoding Myc protein) is associated with cell cycle progression. Lack of c-myc expression permits cells to withdraw from the cell cycle and cease differentiating. Furthermore, constitutive c-myc expression promotes continuous cell cycle progression independent of growth factors (Rapp et al., 1985, Nature 317:434–438). Over-expression of c-myc is a common characteristic of many (if not most) human tumors. Prior art studies have correlated c-myc expression and odc expression in human tumors, but not in surrounding normal (i.e. non-tumor) tissue (Gan et al., 1993, J. Histochem. Cytochem. 41:1185–1196; Mori et al., 1996, Cancer 77{8 Suppl.}:1634:1638; Mimori et al., 1997, Dis. Colon Rectum 40:1095–1100). These studies suggest that deregulation of c-myc expression may lead to deregulation of odc expression.

Numerous stimuli are known which induce deregulation of c-myc expression (Schwab et al., 1984, Proc. Natl. Acad. Sci. USA 81:4940–4944; Payne et al., 1982, Nature 295:209–214; Klein et al., 1985 Immunol. Today 6:208–215). Because deregulated Myc transactivates odc expression, these stimuli can be predicted to induce deregulation of odc expression in general. However, until the present invention, it has not been known whether either of the alleles of odc is more susceptible to transactivation by Myc, and thus the genetic component of carcinogenic susceptibility of an individual could not be ascertained.

BRIEF SUMMARY OF THE INVENTION

The invention relates to a method of assessing the relative susceptibility of a mammal (e.g. a human) to an epithelial cancer. The epithelial cancer can, for example be a skin cancer (e.g. a squamous cell carcinoma), a cancer of the digestive system, an esophageal cancer, a gastric cancers, a colon cancer, a prostate cancer, a breast cancer, an hematopoietic cancer, a lung cancer, a melanoma, or a cervical cancer. The method comprises determining whether the mammal comprises an A-allele of the odc gene. If the mammal comprises the A-allele, then the mammal has a greater susceptibility to the epithelial cancer than a mammal of the same type which does not comprise the A-allele.

In one embodiment, determining whether the mammal comprises an A-allele of the odc gene comprises amplifying a reference portion of the mammal's genome. By way of example, the reference portion can be amplified using a pair of primers having nucleotide sequences SEQ ID NO: 3 and SEQ ID NO: 4. Optionally, the reference portion can be further amplified using a pair of nested primers having nucleotide sequences SEQ ID NO: 5 and SEQ ID NO: 6. The reference portion preferably comprises a region (e.g. intron 1) of the odc gene, such as nucleotide residues +282 to +340 relative to the transcription start site. The reference portion can, for example, have a nucleotide sequence selected from the group consisting of SEQ ID NO: 1 and SEQ ID NO: 2. The region preferably comprises the nucleotide residue located at position +321 relative to the transcription start site.

An oligonucleotide probe can be annealed with a target portion of the mammal's genome prior to amplifying the reference portion. The target portion includes the nucleotide residue located at position +321 relative to the transcription start site of the odc gene. The probe can, optionally, comprise a fluorescent label such as FAM, TET, rhodamine, VIC, JOE, or Hex. The probe can further comprise a fluorescence quencher such as TAMRA or DABCYL. For example, the probe can have the nucleotide sequence SEQ ID NO: 14 and comprise both a fluorescent label and a fluorescent quencher When the probe comprises both the label and the quencher, one is preferably attached to the probe within 10 nucleotide residues of the 3'-end of the probe and the other is preferably attached to the probe within 10 nucleotide residues of the 5'-end of the probe. The reference portion can be amplified using a DNA polymerase having 5'→3' exonuclease activity, such as *Thermus aquaticus* DNA polymerase. Preferably, the probe has a length from 15 to about 30 nucleotide residues and the size of the reference portion is not more than about 100 nucleotide residues.

In another embodiment of this method of the invention, determining whether the mammal comprises an A-allele of the odc gene comprises contacting a polynucleotide derived from the mammal's genome with a molecular beacon probe. The probe has a targeting portion which is complementary to a target region of the odc gene, and the target region includes the nucleotide residue located at position +321 relative to the transcription start site of the odc gene. Preferably, the targeting portion is completely complementary to the target region of the A-allele of the odc gene and has a length from about 20 to about 40 nucleotide residues. For example, the targeting portion of the first probe can have the nucleotide sequence SEQ ID NO: 14, and the targeting portion of the second probe can have the nucleotide sequence SEQ ID NO: 15. The target region can, for example, comprise about 20 to about 30 consecutive nucleotide residues of a polynucleotide having a sequence selected from the group consisting of SEQ ID NOs: 1 and 2. The polynucleotide can, for example, be selected from the group consisting of a chromosome of the mammal, a chromosomal fragment of the mammal, and an amplified portion of the genome of the mammal. Optionally, the method of this embodiment can further comprise contacting the polynucleotide with a second molecular beacon probe. The second probe has a targeting portion which is completely complementary to a target region of the G-allele of the odc gene.

The invention also relates to an isolated polynucleotide having a length of at least about 15 nucleotide residues and being either homologous with or complementary to a portion of a mammalian (e.g. human) odc gene. The portion of the odc gene includes the nucleotide residue at position +321, relative to the transcription start site of the odc gene. In one embodiment, that nucleotide residue is a guanine residue. By way of example, the isolated polynucleotide can have the nucleotide sequence of one of SEQ ID NOs: 14 and 15.

The invention further relates to a kit for assessing the susceptibility of a mammal to an epithelial cancer. The kit comprises a first oligonucleotide probe which anneals specifically with target portion of the mammal's genome and a first primer for amplifying a reference portion of the odc gene. The target portion includes the nucleotide residue located at position +321 relative to the transcription start site of the odc gene. The first probe comprises a fluorescent label and a fluorescence quencher attached to separate nucleotide residues thereof. The reference portion also includes the nucleotide residue located at position +321 relative to the transcription start site of the odc gene. The kit can further comprise a DNA polymerase having 5'→3' exonuclease activity. In one embodiment, the first probe is completely complementary to the target portion if the nucleotide residue located at position +321 is A, and the kit further comprises a second oligonucleotide probe which is completely complementary to the target portion if the nucleotide residue located at position +321 is G and a second primer for performing PCR amplification of at least the target portion in conjunction with the first primer. For example, the kit can comprise first and second oligonucleotide probes having nucleotide sequences SEQ ID NOs: 14 and 15, first and second amplification primers having nucleotide sequences SEQ ID NOs: 12 and 13, and Taq DNA polymerase.

In another aspect, the invention relates to a method of assessing whether a test compound is an inhibitor of carcinogenesis. This method comprises assessing ornithine decarboxylase activity in a cell comprising an A-allele of the human odc gene in the presence of a inducer of carcinogenesis and in the presence or absence of the test compound. If ornithine decarboxylase activity is lower in the presence of the test compound than in the absence of the test compound, then the test compound is an inhibitor of carcinogenesis.

The invention also relates to a method of assessing whether a test compound is a inducer of carcinogenesis. This method comprises assessing ornithine decarboxylase activity in a cell comprising an A-allele of the human odc gene in the presence of a inducer of carcinogenesis and in the presence or absence of the test compound. If ornithine decarboxylase activity is greater in the presence of the test compound than in the absence of the test compound, then the test compound is a inducer of carcinogenesis.

BRIEF DESCRIPTION OF THE DRAWINGS

FIG. 2, comprising FIGS. 2A (SEQ ID NO: 1) and 2B (SEQ ID NO: 2) are the nucleotide sequences of the A- and G-alleles, respectively, of a region of the human odc gene extending from nucleotide residues +282 to +340, relative to the transcription start site. An asterisk marks the location of the single nucleotide polymorphism at nucleotide residue +321 that differentiates the two alleles.

DETAILED DESCRIPTION

It is known in the art that two alleles of the odc gene are found in the human population. However, the functional significance of the presence of the two alleles has not previously been appreciated by others. The present invention is based on the discovery that the presence of the minor (i.e. less frequently occurring) allele of the odc gene (herein designated "the A-allele") in an individual, and particularly the presence of two copies of the minor allele in an individual, is predictive of a high incidence of carcinogenesis in the individual. The presence of the minor allelic allele in human individuals is, for example, highly predictive of the individual's susceptibility to development of environmentally-induced squamous cell carcinoma and other epithelial cancers (e.g. skin cancers).

Definitions

The articles "a" and "an" are used herein to refer to one or to more than one (i.e. to at least one) of the grammatical object of the article. By way of example, "an element" means one element or more than one element.

As used herein, a mammal "comprises an A-allele of the odc gene" if the genome of the mammal comprises one or more copies of the A-allele.

A mammal is "homozygous" for the A-allele of the odc gene if the genome of the mammal comprises at least two copies of the A-allele.

The "A-allele" of the odc gene means a mammalian odc gene having an adenine residue at position +321 relative to the transcriptional start site. The A-allele of the odc gene is also referred to herein as "the minor allele" of odc.

The "G-allele" of the odc gene means a mammalian odc gene having a guanine residue at position +321 relative to the transcriptional start site. The G-allele of the odc gene is also referred to herein as "the major allele" of odc.

A polynucleotide is "derived" from the genome of a mammal if the polynucleotide is homologous with or complementary to at least a portion of the mammal's genome. By way of example, polynucleotides derived from a mammalian genome include, a chromosome, a chromosomal fragment, a processed or non-processed mRNA, a cDNA made from a processed or non-processed mRNA, and a synthetic polynucleotide complementary to or homologous with a portion of one of these polynucleotides.

An "isolated polynucleotide" refers to a synthetic nucleic acid segment or a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the polynucleotide, e.g, RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is anti-parallel to the first region if the residue is thymine or uracil. Similarly, it is known that a cytosine residue of a first nucleic acid strand is capable of base pairing with a residue of a second nucleic acid strand which is anti-parallel to the first strand if the residue is guanine. A first region of a nucleic acid is complementary to a second region of the same or a different nucleic acid if, when the two regions are arranged in an anti-parallel fashion, at least one nucleotide residue of the first region is capable of base pairing with a residue of the second region. Preferably, the first region comprises a first portion and the second region comprises a second portion, whereby, when the first and second portions are arranged in an anti-parallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A first region of an oligonucleotide "flanks" a second region of the oligonucleotide if the two regions are adjacent one another or if the two regions are separated by no more than about 1000 nucleotide residues, and preferably no more than about 100 nucleotide residues.

A second set of primers is "nested" with respect to a first pair of primers if, after amplifying a nucleic acid using the first pair of primers, each of the second pair of primers anneals with the amplified nucleic acid, such that the amplified nucleic acid can be further amplified using the second pair of primers.

As used herein, an "instructional material" includes a publication, a recording, a diagram, or any other medium of expression which can be used to communicate the usefulness of the composition of the invention for performing a method of the invention or for associating the presence of an A-allele of the odc gene in a mammal with carcinogenic susceptibility. The instructional material of the kit of the invention can, for example, be affixed to a container which contains a kit of the invention or be shipped together with a container which contains the kit. Alternatively, the instructional material can be shipped separately from the container with the intention that the instructional material and the kit be used cooperatively by the recipient.

The terms "polynucleotide" and "oligonucleotide" are used interchangeably herein.

Description

The invention includes a method of assessing the relative susceptibility of a mammal (e.g. a human) to an epithelial cancer such as a skin cancer (e.g. a squamous cell carcinoma). The 'relative' susceptibility of a mammal to the epithelial cancer refers to the fact that, among a population of individuals exposed to equivalent carcinogenic stimuli, some individuals are more likely to develop epithelial cancers than others. This differential carcinogenic potential is attributable, at least in part to the genetic makeup of the individuals in the population. Germ-line mutations in tumor suppressor genes (e.g. Rb, p53, BRCA1, WT1, and the like) are one mechanism to which the genetic contribution to carcinogenic potential may be attributed. However, germ-line mutations in tumor suppressor genes are relatively rare in large populations, and cannot alone account for the genetic contribution to carcinogenic potential.

Mutations in other genes, such as genes encoding proteins involved in metabolism of carcinogens and DNA repair, have been implicated in carcinogenesis. However, even genes not involved in tumor suppression, carcinogen metabolism, or DNA repair can affect susceptibility to carcinogenesis. For example, the gene (odc) encoding ornithine decarboxylase may, by affecting cellular polyamine levels, affect the susceptibility of cells to carcinogenesis, as described (Soler et al., 1998, Cancer Res. 58:1654–1659). It has not previously been known whether the presence in the genome of an individual of one of the two alleles of the odc gene renders the individual more susceptible to carcinogenesis than an individual having a genome which does not comprise the minor allele.

The present invention is based on the discovery that the presence in the genome of an A-allele of the odc gene is correlated with greater susceptibility to carcinogenesis in mammals, particularly in humans. The effect is furthermore dose-dependent, meaning that a first individual who is homozygous for the A-allele has a greater susceptibility than a second individual who is heterozygous for the A- and G-alleles, and that the second individual has a greater susceptibility than a third individual who is homozygous for the G-allele. Thus, the method of the invention for assessing the relative susceptibility of a mammal to an epithelial cancer comprises determining whether the mammal comprises an A-allele of the odc gene. If the mammal comprises the A-allele, then the mammal has a greater susceptibility to the epithelial cancer than a mammal of the same type which does not comprise the A-allele. The invention preferably comprises determining whether the mammal is homozygous for the A-allele, heterozygous for the A- and G-alleles, or homozygous for the G-allele because, as noted above, the carcinogenic susceptibility attributable to these genotypes differs.

Substantially any method of detecting an allele of the odc gene can be used including, for example, hybridization, amplification, or sequencing methods. For example, a PCR/RFLP method can be used to determine whether the mammal is homozygous for the A-allele, heterozygous for the A- and G-alleles, or homozygous for the G-allele. This PCR/ RFLP method relies on the fact that the A-allele of the odc gene comprises a PstI restriction endonuclease cleavage site at nucleotide residues +317 to +322, relative to the transcription start site, while the G-allele does not. The size of restriction fragments generated by treating a polynucleotide comprising residues +317 to +322 of the odc gene with restriction endonuclease PstI thus depends on whether the polynucleotide is derived from an A-allele or a G-allele of the gene. If the polynucleotide is derived from an A-allele, there will be one more restriction fragment following reaction with PstI than if it is derived from a G-allele.

The PCR/RFLP method of the invention thus comprises amplifying a portion of the odc gene (comprising nucleotide residues +317 to +322) of a mammal, treating the amplified portion with PstI, and observing at least one of the size and the number of restriction fragments so generated. Acceptable buffers and reaction conditions for amplification and restriction endonucleolytic digestion are well known in the art. By way of example, if the odc gene of a human individual is amplified using a nested pair of primers (e.g. using a first pair of primers having sequences SEQ ID NOs: 3 and 4 and then a second pair of primers having sequences SEQ ID NOs: 5 and 6), a 546-nucleotide-residue portion is amplified. Treatment of this amplified portion with PstiI yields a (non-cleaved) 546-nucleotide-residue polynucleotide if the portion was derived from a G-allele and both 351- and 195-nucleotide-residue polynucleotides if the portion was derived from an A-allele. If both alleles from the individual are amplified and treated together, only a 546-nucleotide-residue polynucleotide will be observed if the individual is homozygous for the G-allele, a mixture (ca. 1:1) of 351- and 195-nucleotide-residue polynucleotides will be observed if the individual is homozygous for the A-allele, and a mixture (ca. 1:1:1) of 351-, 195-, and 546-nucleotide-residue polynucleotides will be observed if the individual is heterozygous for the A- and G-alleles.

Another method of determining whether the individual mammal comprises an A-allele of the odc gene comprises amplifying and sequencing a reference portion of the mammal's genome. The reference portion includes at least a region of the odc gene, preferably including both alleles from the individual. The region includes at least the nucleotide residue at position +321 relative to the transcription start site of the odc gene, since this residue differs between the A- and G-alleles (the residue is adenine in the A-allele and guanine in the G-allele).

The reference portion of the odc gene can be amplified, for example, using standard PCR primers which anneal with complementary strands at positions flanking the region. Alternatively, nested pairs of primers can be used to specifically amplify the region of the odc gene. By way of example, the region of the human odc gene can be amplified using a first pair of primers having the nucleotide sequences SEQ ID NOs: 3 and 4, using a second pair of primers having the nucleotide sequences SEQ ID NOs: 5 and 6, or using both the first and second pairs of primers.

When the human odc gene is amplified using the second pair of primers (alone or in conjunction with the firs pair of primers), the amplified region will comprise the nucleotide sequence SEQ ID NO: 1 if the gene is the A-allele or the nucleotide sequence SEQ ID NO: 2 if the gene is the G-allele. When both alleles from an individual are amplified together, the amplified regions will comprise the nucleotide sequence SEQ ID NO: 1, but not SEQ ID NO: 2, if the individual is homozygous for the A-allele. The amplified regions will comprise the nucleotide sequence SEQ ID NO: 2, but not SEQ ID NO: 1, if the individual is homozygous for the G-allele. The amplified regions will comprise a mixture of polynucleotides, some having the nucleotide sequence SEQ ID NO: 1 and other having the nucleotide sequence SEQ ID NO: 2 if the individual is heterozygous for the A- and G-alleles. The odc genotype of the individual can thereby be determined. SEQ ID NOs: 1 and 2 are listed in FIGS. 2A and 2B, respectively.

A requirement that amplified genomic regions of individuals be sequenced can be detrimental to the efficiency and practicality of a large-scale (i.e. "high-throughput") screening effort. Thus, if the odc genotypes of large numbers (i.e. more than about 50 to 500) of individuals are to be determined, it is preferable to use a screening method that does not require sequencing of individual amplified nucleic acids. An example of one such method is now described.

Figure 1:
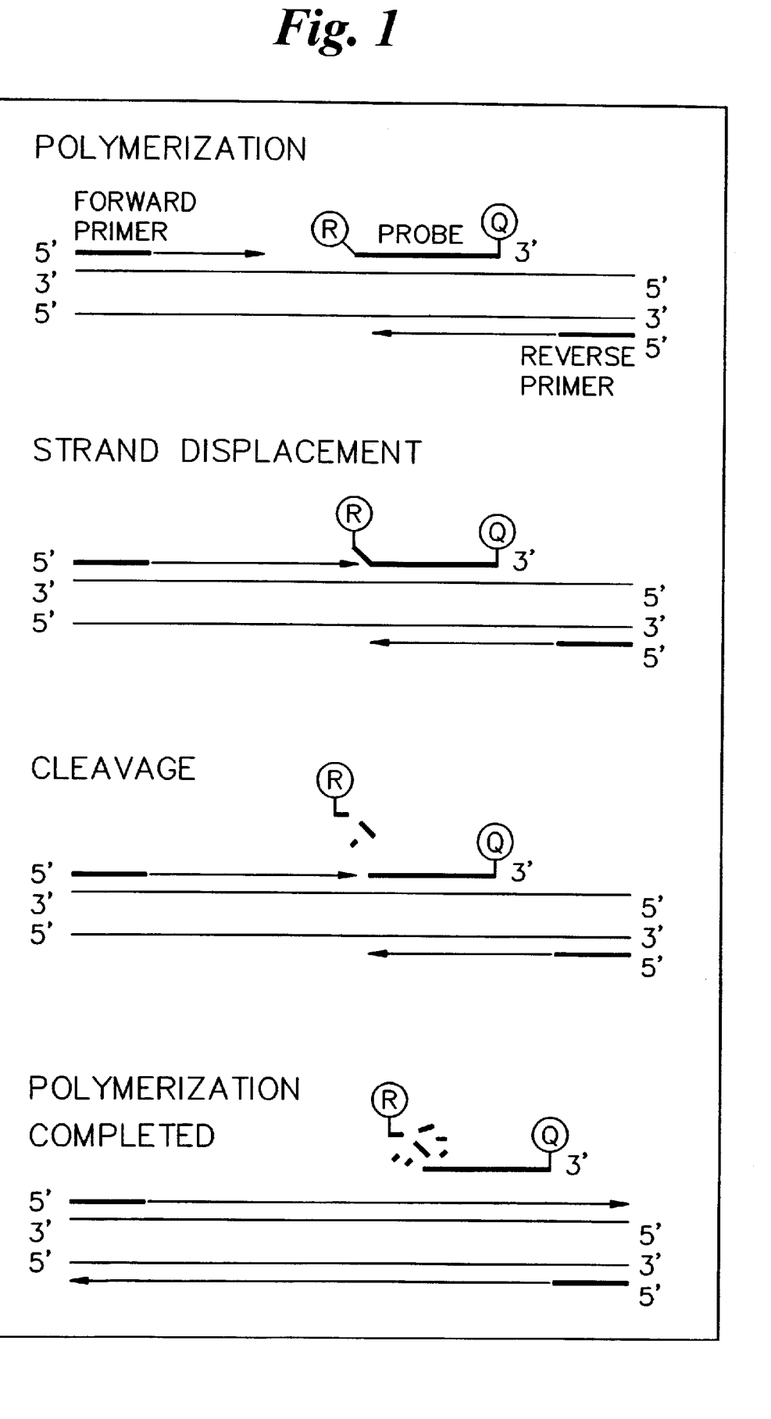
FIG. 1 is a diagram depicting an embodiment of the allelic assessment of the invention, as described herein. "R" (reporter) refers to a fluorescent label (e.g. a dye such as VIC, FAM, TET, JOE, or HEX), and "Q" (quencher) refers to a fluorescence quencher (e.g. TAMRA).

The invention includes an allelic discrimination method for identifying the odc genotype of an individual mammal (e.g. a human). A summary of this method is depicted in FIG. 1. The allelic discrimination method of the invention involves use of a first oligonucleotide probe which anneals with a target portion of the mammal's genome. The target portion comprises a portion of the odc gene of the mammal, including the nucleotide residue at position +321 relative to the transcription start site. Because the nucleotide residue at this position differs in the A-allele and the G-allele, the first probe is completely complementary to only one of the two alleles. Alternatively, a second oligonucleotide probe can also be used which is completely complementary to the target portion of the other of the two alleles. The allelic discrimination method of the invention also involves use of at least one, and preferably a pair of amplification primers for amplifying a reference region of the odc gene of the mammal. The reference region includes at least a portion of the target portion, and preferably includes the nucleotide residue at position +321 of the odc gene.

The allelic discrimination method of the invention is performed by annealing the first probe with the target portion of an odc gene obtained from an individual mammal and amplifying the reference region of the odc gene, which comprises at least part of the target portion. Alternatively, both the first and the second probe can be annealed with the target portion in order to achieve completely complementary annealing of a probe to each target portion.

Because the reference region and the target portion overlap by at least one base, preferably by at least about half the length of the target portion, and more preferably completely overlap, the enzyme (e.g. *Thermus aquaticus* {Taq} DNA polymerase) which catalyzes the amplification reaction and the first (or second) probe will collide. If the probe is not completely complementary to the target portion, it is more likely to dissociate from the target portion upon collision than if it is completely complementary. Therefore, unless the enzyme exhibits 5'→3' exonuclease activity, amplification ceases or is greatly inhibited.

If the enzyme which catalyzes the amplification reaction exhibits 5'→3'exonuclease activity (e.g. Taq DNA polymerase), then the enzyme will at least partially degrade the 5'-end of a probe with which it collides unless the probe dissociates from the target portion upon collision with the enzyme. As noted above, if the probe is not completely complementary to the target portion, it is much more likely to dissociate from the target portion upon collision than if it is completely complementary. If a detectable label is attached to a nucleotide residue at or near the 5'-end of the probe, release of the detectable label from the probe can be used as an indication that the enzyme and probe have collided and that the probe did not dissociate from the target portion. Thus, release of the detectable label from the probe upon amplification of the region indicates that the probe was completely complementary to the target portion. By selecting either or both of a probe completely complementary to the target portion of the A-allele of the odc gene and a probe completely complementary to the target portion of the G-allele of the gene and assessing release of the label from the probe(s), the identity of the allele(s) can be ascertained.

The probe is preferably a DNA oligonucleotide having a length in the range from about 20 to about 40 nucleotide residues, preferably from about 20 to about 30 nucleotide residues, and more preferably having a length of about 25 nucleotide residues. In one embodiment, the probe is rendered incapable of extension by a PCR-catalyzing enzyme such as Taq polymerase, for example by having a fluorescent probe attached at one or both ends thereof. Although non-labeled oligonucleotide probes can be used in the kits and methods of the invention, the probes are preferably detectably labeled. Exemplary labels include radionuclides, light-absorbing chemical moieties (e.g. dyes), fluorescent moieties, and the like. Preferably, the label is a fluorescent moiety, such as 6-carboxyfluorescein (FAM), 6-carboxy-4,7,2',7'-tetrachlorofluoroscein (TET), rhodamine, JOE (2,7-dimethoxy-4,5-dichloro-6-carboxyfluorescein), or HEX (hexachloro-6-carboxyfluorescein).

In a particularly preferred embodiment, the probe of the invention comprises both a fluorescent label and a fluorescence-quenching moiety such as 6-carboxy-N,N,N',N'-tetramethylrhodamine (TAMRA, or 4-(4'-dimethlyaminophenylazo)benzoic acid (DABCYL). When the fluorescent label and the fluorescence-quenching moiety are attached to the same oligonucleotide and separated by no more than about 40 nucleotide residues, and preferably by no more than about 30 nucleotide residues, the fluorescent intensity of the fluorescent label is diminished. When one or both of the fluorescent label and the fluorescence-quenching moiety are separated from the oligonucleotide, the intensity of the fluorescent label is no longer diminished. Preferably, the probe of the invention has a fluorescent label attached at or near (i.e. within about 10 nucleotide residues of) one end of the probe and a fluorescence-quenching moiety attached at or near the other end. Degradation of the probe by a PCR-catalyzing enzyme releases at least one of the fluorescent label and the fluorescence-quenching moiety from the probe, thereby discontinuing fluorescence quenching and increasing the detectable intensity of the fluorescent label. Thus, cleavage of the probe (which, as discussed above, is correlated with complete complementarity of the probe with the target portion) can be detected as an increase in fluorescence of the assay mixture.

If detectably different labels are used, more than one labeled probe can be used. For example, the assay mixture can contain a first probe which is completely complementary to the target portion of the A-allele of the odc gene and to which a first label is attached, and a second probe which is completely complementary to the target portion of the G-allele, as described herein in Example 2. When two probes are used, the probes are detectably different from each other, having, for example, detectably different size, absorbance, excitation, or emission spectra, radiative emission properties, or the like. For example, a first probe can be completely complementary to the target portion of the A-allele and have FAM and TAMRA attached at or near opposite ends thereof. The first probe can be used in the method of the invention together with a second probe which is completely complementary to the target portion of the G-allele and has TET and TAMRA attached at or near opposite ends thereof. Fluorescent enhancement of FAM (i.e. effected by cessation of fluorescence quenching upon degradation of the first probe by Taq polymerase) can be detected at one wavelength (e.g. 518 nanometers), and fluorescent enhancement of TET (i.e. effected by cessation of fluorescence quenching upon degradation of the second probe by Taq polymerase) can be detected at a different wavelength (e.g. 582 nanometers).

It is important that the probe exhibit a melting temperature (Tm) within the range from about 60 to 70° C., more preferably in the range from 65 to 67° C. Furthermore, because each probe is completely complementary to only one of the A- and G-alleles of the odc gene, each probe will necessarily have at least one nucleotide residue which is not complementary to the corresponding residue of the other allele. This non-complementary nucleotide residue of the probe is preferably located near the midsection of the probe (i.e. within about the central third of the probe sequence) and is preferably approximately equidistant from the ends of the probe. Thus, for example, the probe which is completely complementary to the A-allele of the human odc gene can, for example, be completely complementary to nucleotide residues +310 to +329 of the A-allele, relative to the transcription start site. Because the A- and G-alleles differ at position +321, this probe will have a mismatched base pair nine nucleotide residues from one end when it is annealed with the corresponding target portion of the G-allele.

By way of example, labeled probes having the sequences SEQ ID NOs: 14 and 15 can be used, in conjunction with amplification probes having sequences SEQ ID NOs: 12 and 13 in order to determine the allelic content of a mammal (i.e. to assess whether the mammal comprises one or both of an A allele and a G allele of odc).

The size of the reference portion which is amplified according to the allelic discrimination method of the invention is preferably not more than about 100 nucleotide residues. It is also preferred that the Tm for the amplified reference portion with the genomic DNA or fragment thereof be in the range from about 57 to 61° C., where possible.

It is understood that binding of the probe(s) and primers and that amplification of the reference portion of the odc gene according to the allelic discrimination method of the invention will be affected by, among other factors, the concentration of $Mg^{++}$ in the assay mixture, the annealing and extension temperatures, and the amplification cycle times. Optimization of these factors requires merely routine experimentation and is well within the ken of the skilled artisan.

The invention further includes another allelic discrimination method. The probes used in this method are generally known as "molecular beacons." Molecular beacon probes are single-stranded oligonucleotides having a fluorescent label (e.g. rhodamine, FAM, TET, VIC, JOE, or HEX) attached to the 5'-end thereof and a fluorescence quencher (e.g. TAMRA or DABCYL) attached to the 3'-end thereof (or vice versa), as described (Kostrikis et al., 1998, Science 279:1228–1229). The sequence of each molecular beacon probe is selected to include two complementary hairpin regions, whereby the probe can self-anneal to form a hairpin structure. The 5'- and 3'-ends are brought into close association when the hairpin structure forms. The probe also comprises a targeting portion which is selected to be complementary to a target sequence (e.g. a single allele of a gene). The targeting portion and at least one of the hairpin regions are located in close proximity to one another, meaning that the targeting portion either overlaps the hairpin region or flanks it, having no more than about 5 nucleotide residues therebetween.

If the hairpin regions of the molecular beacon probe anneal with one another, then the probe does not fluoresce, because the hairpin structure forms and the fluorescence quencher attached to one end of the probe quenches fluorescence of the label attached to the other end of the probe. If the targeting portion of the probe anneals with a region of a nucleic acid having the target sequence, then formation of the hairpin structure is inhibited, the fluorescence quencher is not brought into association with the fluorescent label, and the probe fluoresces. Multiple molecular beacon probes can be used in a single reaction mixture, and fluorescence associated with the probes can be differentiated if, for example, the labels attached to the probes are detectably different (e.g. fluorescent emissions from the dyes have different wavelengths). For example, using a first molecular beacon probe which anneals specifically with one allele of a gene (e.g. odc) and a second, differently labeled molecular beacon probe which anneals specifically with the other allele, it is possible to differentiate individuals homozygous for the one allele, individuals homozygous for the other allele, and individuals heterozygous for the two alleles.

Thus, according to this method of the invention, a molecular beacon probe is used which has a targeting portion which is complementary to a target region (e.g. 20 to 40 nucleotide residues, more preferably 20 to 30 residues) of the odc gene, the target region including, and preferably being approximately centered around, nucleotide +321, relative to the transcription start site. More preferably, two such probes are used, one having a targeting region completely complementary to the target region of the A-allele of the odc gene, and the other having a targeting region completely complementary to the target region of the G-allele.

The method of determining whether the mammal comprises an A-allele of the odc gene using a molecular beacon probe comprises contacting a polynucleotide derived from the mammal's genome with the probe. The probe has a targeting region which is complementary (preferably completely complementary) to a target region of one allele the mammal's odc gene. The target region includes the nucleotide residue located at position +321, relative to the transcription start site. If the targeting region is complementary to the target region of at least one allele of the odc gene of the mammal, then the probe fluoresces; otherwise, it does not fluoresce. Two such probes can be used (e.g. one completely complementary to the target region of the A-allele and the other completely complementary to the target region of the G-allele), and if the two probes are detectably different (e.g. they have fluorescent labels which fluoresce at different wavelengths) then the presence of two alleles can be simultaneously assayed.

Of course, it is understood that any method of ascertaining the genotype of an individual mammal at the odc locus can be used to assess the relative susceptibility of the individual to an epithelial cancer. Thus, the invention includes known methods (both those described herein and those not explicitly described herein) and allelic discrimination methods which may be hereafter developed.

The invention also includes a kit for assessing the susceptibility of a mammal to an epithelial cancer according to the one or more of the methods of the invention. The kit comprises a plurality of reagents useful for performing one of the methods, and optionally further comprises an instructional material which describes how the method is performed, the association between the presence of the A-allele and carcinogenic susceptibility, or both. The instructional material of the kit of the invention can, for example, be affixed to a container which contains one or more reagents used in a method of the invention or be shipped together with a container which contains the reagent(s). Alternatively, the instructional material can be shipped separately from the container with the intention that the instructional material and the reagent(s) be used cooperatively by the recipient.

By way of example, a kit for performing the allelic discrimination method of the invention comprises:

a) a first oligonucleotide probe which anneals specifically with target portion of the mammal's genome, wherein the target portion includes the nucleotide residue located at position +321 relative to the transcription start site of the odc gene, the probe comprising a fluorescent label and a fluorescence quencher attached to separate nucleotide residues thereof, and b) a primer for amplifying a reference portion of the odc gene, the reference portion including the nucleotide residue located at position +321 relative to the transcription start site of the odc gene. The kit can further comprise a DNA polymerase having 5→3' exonuclease activity. The kit can also comprise a second oligonucleotide probe having a different annealing specificity than the first (e.g. wherein the first is completely complementary to the target portion of the A allele and the second is completely complementary to the target portion of the G allele), a second primer (e.g. such that this and the other primer can be used to amplify at least the target portion by a PCR), or both. The kit can comprise an instructional material which can, for example, describe performance of the allelic discrimination method, the association between the presence of the A-allele and carcinogenic susceptibility, or both The invention includes another kit, this kit comprising at least one, and preferably two molecular beacon probes, as described herein. When the kit comprises two molecular beacon probes, one is preferably specific for (i.e. completely complementary to the a region including nucleotide residue +321 of) the A-allele of the odc gene, and the other is specific for the G-allele. This kit can further comprise an instructional material, as described above.

The invention also includes a screening method of assessing whether a test compound is an inhibitor of carcinogenesis. Because it has been discovered, as described herein, that it is the A-allele of the odc gene which is most strongly correlated with carcinogenic susceptibility, discovery of agents which inhibit expression of this allele specifically (i.e. without inhibiting expression of the G-allele as severely) is useful for development of carcinogenesis-inhibiting pharmaceutical and other compositions. This screening method comprises assessing ornithine decarboxylase activity in a cell which comprises an A-allele of the human odc gene. The cell is preferably homozygous for the A-allele. Ornithine decarboxylase activity is assessed in the presence of a inducer of carcinogenesis and in the presence or absence of the test compound. If ornithine decarboxylase activity is lower in the presence of the test compound than in the absence of the test compound, then the test compound is an inhibitor of carcinogenesis. If ornithine decarboxylase activity is greater in the presence of the test compound than in the absence of the test compound, then the test compound is a inducer of carcinogenesis. This screening method can optionally include a step wherein a cell or cell line comprising an A-allele of the odc gene is selected prior to contacting the cell with the test compound and assessing ornithine decarboxylase activity of the cell. Optionally, a cell which is homozygous for the G-allele of odc can be treated identically, and ornithine decarboxylase activity of this cell assessed as a control. If the test compound has a different effect on ornithine decarboxylase activity in the cell comprising the A-allele than on the same activity in the cell comprising the G-allele, then this is an indication that the effects of the test compound on mammalian cells will depend on the genotype of the mammalian cells.

Although the descriptions provided herein are principally directed to kits and methods which are applicable to human cancers, it will be understood by the skilled artisan that such methods and kits are generally applicable to cancers of mammals of all sorts. Modification, where necessary, of the kits and methods of the invention to conform to non-human cancers is well understood, and the ordinarily skilled veterinary worker can design and perform such modification with merely ordinary, if any, experimentation. Representative mammals include, for example, primates, cattle, pigs, horses, sheep, cats, and dogs.

The kits and methods described herein are applicable for substantially any epithelial cancer, including, for example, skin cancers such as squamous cell carcinoma. Other epithelial cancers for which the compositions, kits, and methods described herein can be used include cancers of the digestive system, esophageal cancers, gastric cancers, colon cancers, prostate cancers, breast cancers, hematopoietic cancers, lung cancers, melanomas, and cervical cancers.

It is believed that the nucleotide sequence of the G-allele of the human odc gene has not been previously described. The invention therefore includes an isolated polynucleotide which is homologous with or complementary to the G-allele of the odc gene, wherein the polynucleotide is homologous with or complementary to, respectively, the nucleotide residue at position +321, relative to the transcription start site. Such polynucleotides include, for example, cDNA generated from a mammalian (e.g. human) transcript of the odc gene or a probe which is complementary to or homologous with a portion of the odc gene including nucleotide residue +321. Examples of such a polynucleotide include a polynucleotide having the nucleotide sequence SEQ ID NO: 2, a polynucleotide having the nucleotide sequence SEQ ID NO: 10, or a polynucleotide having the nucleotide sequence SEQ ID NO: 11. The polynucleotide has a length of at least about 15 nucleotide residues, and is preferably in the range from about 20 to 100 residues, from 20 to 40 residues, or more preferably, 20 to 30 (e.g. 25) nucleotide residues. The invention also includes analogous isolated polynucleotides corresponding to the A-allele of the odc gene.

The invention is now described with reference to the following Examples. These Examples are provided for the purpose of illustration only, and the invention is not limited to these Examples, but rather encompasses all variations which are evident as a result of the teaching provided herein.

EXAMPLE 1

Others (Hickok et al., 1987, DNA 6:179–187) have observed that approximately 50% of human.individuals are homozygous for the major allele of the odc gene (herein designated the G-allele) and approximately the remainder are heterozygous for the G-allele and the minor allele of the odc gene, herein the A-allele. A nested PCR/RFLP assay was used to confirm this analysis in 51 human individuals. The results of this assay are listed in Table 1.

TABLE 1

| Number of Individuals | Genotype[1] | % of All Individuals |
| --- | --- | --- |
| 33 | GG | 65.7 |
| 16 | AG | 31.4 |
| 2 | AA | 3.9 |

Notes:
[1]G means a G-allele of the odc gene; A means an A-allele of the odc gene.

The PCR/RFLP assay was performed as follows. Genomic DNA was obtained from individuals. A 756-nucleotide-residue fragment containing the PstI site at +317 to +322 (relative to the transcription start site) of the odc gene was amplified using a first pair of primers, and then amplified using a second pair of (nested) primers to yield a 546-nucleotide-residue amplified fragment. The nucleotide sequences of the first pair of primers were: 5'-ATCGTGGCTG GTTTGAGCTG-3' (SEQ ID NO: 3) and 5'-GTCATCTGCT CTGTAGACAC AGCG-3' (SEQ ID NO: 4). Amplification using the first pair of primers yielded a fragment having a length of about 756 nucleotide residues. The nucleotide sequences of the second pair of primers were: 5'-GGTGCTATAA GTAGGGAGCG CC-3' (SEQ ID NO: 5) and 5'-CCGAAGGGTT GGGAAAGAGG-3' (SEQ ID NO: 6). Amplification using the second pair of primers yielded a fragment having a length of about 546 nucleotide residues. This amplified fragment was purified from an agarose gel and digested using PstI. The digested amplified fragment preparation was loaded onto an agarose gel and electrophoresed. Amplified fragments obtained from individuals homozygous for the G-allele were not cut by PstI, and exhibited a relative mobility corresponding to the uncut 546-nucleotide-residue fragment. Amplified fragments obtained from individuals homozygous for the A-allele exhibited relative mobilities corresponding to fragments of 351 and 195 nucleotide residues. Amplified fragments obtained from heterozygous individuals exhibited relative mobilities corresponding to fragments of 546, 351, and 195 nucleotide residues.

Figure 2A:
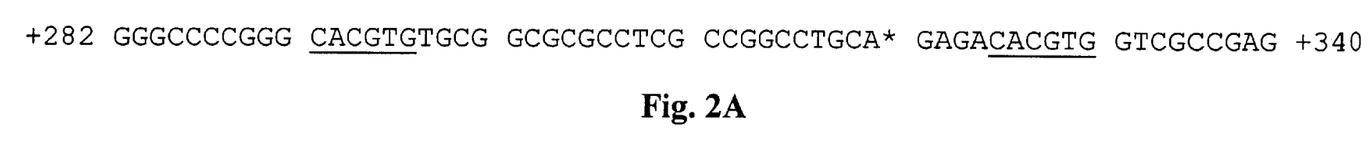
Figure 2B:
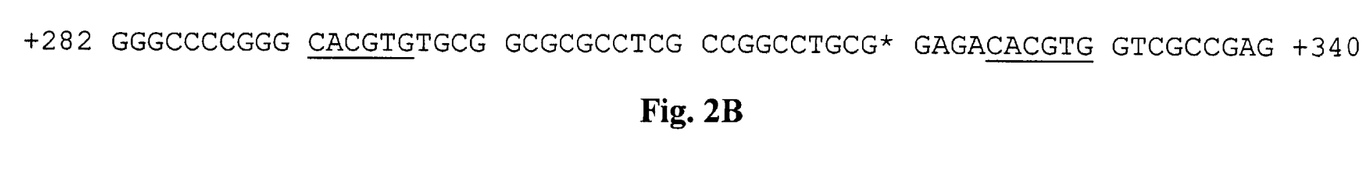

The portion of the human odc gene extending from nucleotide residues +282 to +340 (relative to the transcription start site) was sequenced in individuals homozygous for either the A-allele or the G-allele. The nucleotide sequences of this region for the A- and G-alleles are indicated in FIGS. 2A (SEQ ID NO: 1) and 2B (SEQ ID NO: 2), respectively. The failure of PstI to cleave the G-allele is attributable to the presence of a guanine residue at nucleotide residue +321.

Without wishing to be bound by any particular theory of operation, it is believed that the following discussion explains the increased carcinogenic susceptibility associated with the presence in a mammalian genome of the A-allele of the odc gene, relative to the presence of the G-allele. The single nucleotide polymorphism (SNP) at nucleotide residue +321 is in a very important region of the odc gene. The SNP is within intron 1, close to exon 1. This region contains two Myc-binding domains, designated MB1 and MB2 (Bello-Fernandez et al., 1993, Proc. Natl. Acad. Sci. USA 90:7804–7808). These Myc-binding domains are responsible for the known ability of Myc to transactivate odc effected by binding of Myc/Max heterodimers to these domains. However, binding of Max/Max homodimers does not appear to transactivate odc transcription. Thus, the relative intracellular amounts of Myc, Max, and possibly Mad proteins determine the extent of odc transcription. Clearly, however, Myc/Max heterodimer formation is favored over Max/Max homodimerization (Blackwood et al., 1992, Genes Dev. 6:71–80). It follows that whenever c-myc expression is enhanced, odc expression will also be enhanced.

It is furthermore known that the sequence context surrounding MB 1 and MB2 differentially affects relative binding of Myc/Max and Max/Max dimers (Solomon et al., 1993, Nucl. Acids Res. 21:5372–5376). Binding of Myc/Max dimers is much more sensitive to the nature of the flanking sequences than Max/Max dimers. Bases located −1 to −3, relative to the hexanucleotide core of the binding site (CACGTG; SEQ ID NO: 7) are known to be particularly important for binding, but sequence context further from the core has not been extensively investigated. Recently, the base at position −4 relative to the hexanucleotide core has been shown to influence binding of Myc/Max dimers (Walhout et al., 1998, Biochim. Biophys. Acta 1397:189–201). The SNP in the human odc gene is at position −5, relative to the MB2 domain, and the adenine residue at this position is only found in this human allele. In the rat and mouse genes, there is a guanine residue at this position. Despite the fact that there exists an odc allele with an adenine residue at position +321 (because some humans have a PstI restriction site beginning at base +317), all reported functional analyses of the three human Myc-binding elements (i.e. including the site in the 5'upstream promoter region and the two sites in intron 1) appear to have been made using genes having a guanine residue at nucleotide residue +321. There have been no functional comparisons of the A-allele of the human gene and the G-allele with respect to regulation by c-myc.

In order to determine if the SNP located at nucleotide residue +321 in the human odc gene has functional significance, preliminary gel shift analyses were performed using oligonucleotide probes specific for the A- and G-alleles. In separate experiments, the promoter strength of the A- and G-alleles of human odc (i.e. the ability of these alleles to induce transcriptions of operably linked cDNA encoding luciferase enzyme) were assessed in transfection assays.

Gel shift analyses were performed as follows. Complexes of HeLa cell nuclear proteins and $^{32}$P-labeled oligonucleotide probes were formed by incubating the proteins and probes together at room temperature for 30 minutes. The probes used to detect the A-allele had the nucleotide sequences: 5'-CCGGCCTGCA GAGACACGTG GTCGC-CGAGC G-3' (SEQ ID NO: 8) and 5'-GGCCGGACGT CTCTGTGCAC CAGCGGCTCG C-3' (SEQ ID NO: 9). The probes used to detect the G-allele had the nucleotide sequences: 5'-CCGGCCTGCG GAGACACGTG GTCGC-CGAGC G-3' (SEQ ID NO: 10) and 5'-GGCCGGACGC CTCTGTGCAC CAGCGGCTCG C-3' (SEQ ID NO: 11). These nucleotide sequences correspond to odc nucleotide residues +305 to +336, relative to the transcription start site, and had either an adenine residue (corresponding to the A-allele) or a guanine residue (corresponding to the G-allele) at position +321. Oligonucleotides were end-labeled using T4 polynucleotide kinase and γ-$^{32}$P-ATP.

The electrophoretic mobility shift assays were performed as follows. The assays were performed in 10 microliter reaction mixtures which consisted of 50 millimolar Tris-HCl at pH 7.5, 5 millimolar MgCl$_2$, 2.5 millimolar EDTA, 2.5 millimolar dithiothreitol, 250 millimolar NaCl, 0.25 micrograms per microliter poly-dI:dC, 20% (v/v) glycerol, 5' 10$^5$ to 10' 10$^5$ counts per minute of $^{32}$P-end labeled probes, and an aliquot of HeLa cell nuclear extract containing about 10 micrograms of protein.

The resulting protein-probe complexes were electrophoresed on a non-denaturing 4% (w/v) polyacrylamide gel comprising 0.5' TBE buffer. The electrophoresis procedure indicated that the fragment of the G-allele formed a faster-migrating complex with nuclear proteins than the fragment of the A-allele. Furthermore, there was significantly more binding of nuclear proteins to the probe corresponding to the A-allele. These data demonstrate that the A- and G-alleles do not have identical binding properties with respect to nuclear proteins, suggesting that the two alleles are differentially regulated.

In order to study the functional differences between the A- and G-alleles of odc in vivo, reporter constructs were made. The fragment corresponding to nucleotide residues −462 to +3070 of the human odc gene (relative to the transcription start site) was isolated by PCR from individuals who were homozygous for either the A- or G-allele. The isolated fragments were cloned into the pGL3 plasmid (Promega Corp., Madison, Wis.) and operably linked with a modified firefly luciferase gene. Using a standard calcium phosphate method, NIH 3T3 cells were transient transfected using 1 microgram these constructs together with 0.1 microgram of a renilla luciferase plasmid (pRL; Promega Corp., Madison, Wis.). Both luciferase activities were assayed in cell extract harvested 24 hours post-transfection and in cells transfected with empty pGL3 plasmid as a control.

The results of these assays are listed in Table 2.

TABLE 2

| | Luciferase Activity[1] | | |
|---|---|---|---|
| Experiment # | A-Allele | G-Allele | A/G Allele Ratio |
| 1 | 39.7 | 13.3 | 2.98 |
| 2 | 38.9 | 12.1 | 3.21 |
| 3 | 28.4 | 8.6 | 3.30 |
| 4 | 22.6 | 8.9 | 2.54 |
| 5 | 22.9 | 6.8 | 3.37 |
| | Summary | | 3.08 ± 0.3 (n = 5) |

Notes:
[1]Luciferase activity is expressed as a ratio of firefly luminescence (units per microgram) to renilla luminescence (units per microgram) measured using the same extract.

The magnitude of luciferase activity expressed in transfected cells reflected the relative promoter strength of the promoters of the A- and G-alleles. The results indicated the promoter/intron 1 region of the A-allele yielded consistently greater luciferase expression than did the same region of the G-allele. Presumably, most, if not all, of the odc allele-driven reporter gene expression in these experiments is due to endogenous Myc and Max present in the nuclei of the transfected cells.

EXAMPLE 2

Protocol for ABI Prism™ 7700 Allelic Discrimination of ODC Promoter Region

In this Example, a specific example of a protocol useful for determining the allelic composition of a mammal is provided. This protocol is especially adapted for use with the ABI PRISM™ 7700 Sequence Detection System (PE Biosystems, Foster City, Calif.) and a TaqMan™ (Roche Molecular Systems, Inc., Branchburg, N.J.) PCR reagent kit. In this protocol, the following oligonucleotide primers and probes are used, the oligonucleotides having the indicated melting temperatures (Tm).

"Forward primer":
   5'-CCT GGG CGC TCT GAG GT-3' (Tm=58.4° C.; SEQ ID NO: 12)
"Reverse primer":
   5'-AGG AAG CGG CGC CTC AA-3' (Tm=61.5° C.; SEQ ID NO: 13)
"TaqMan™ Allele A Probe":
   5'-VIC-CAC GTG TCT CTG CAG GCC GG-TAMRA-3' (Tm=66° C.; SEQ ID NO: 14; VIC is a proprietary fluorescent dye available from PE Biosystems; TAMRA is 6-carboxytetramethylrhodamine))
"TaqMan™ Allele G Probe":
   5'-FAM-CAC GTG TCT CCG CAG GCC G-TAMRA-3' (Tm=67° C.; SEQ ID NO: 15; FAM is 6-carboxyfluorescein)

The ABI Prism™ system detects fluorescence which arises from release of a fluorescent dye from a TaqMan™ probe during PCR. For either probe, VIC or FAM can be replaced with JOE (2,7-dimethoxy-4,5-dichloro-6-carboxyfluorescein), with TET (tetrachloro-6-carboxyfluorescein), or with HEX (hexachloro-6-carboxyfluorescein). Each of VIC, FAM, JOE, and HEX is quenched by TAMRA when attached to different residues of an oligonucleotide (e.g. when the dye is attached at one end and TAMRA is attached at the other end).

The protocol is as follows

1) Prepare 5.39 milliliters of a "PCR Master Mix", as indicated in the following table.

| Reagent | Stock Concentration | volume per reaction mixture | volume per 110 reaction mixtures | Final concentration |
|---|---|---|---|---|
| TaqMan ™ Universal PCR Master Mix (PE Biosystems part number 4304437) | 2 x | 25 μl | 2,750 μl | 1 x |
| Forward Primer | 10 μM | 3 μl | 330 μl | 600 nM |
| Reverse Primer | 10 μM | 3 μl | 330 μl | 600 nM |
| TaqMan ™ Allele A Probe | 100 μM | 1.25 μl of a ¹⁄₁₀ dilution | 137.5 μl | 250 nM |
| TaqMan Allele G Probe | 100 μM | 1.25 μl of a ¹⁄₁₀ dilution | 137.5 μl | 250 nM |
| Distilled, deionized water | — | 15.5 μl | 1,705 μl | — |
| Total Volume | — | 49 μl | 5,390 μl | 1 x |

2) Load 49 microliters of the PCR Master Mix into each well of an ABIPrism™ 96-well optical reaction plate (PE Biosystems part number N801-0560).

3) Add 100 nanograms (in 1 microliter volume) of each of three DNA standards (homozygous AA, homozygous GG, and no template controls) individually to eight wells each (i.e. 3 standards×8 wells each=total 24 wells).

4) Load 100 nanograms (in 1 microliter volume) of one or more samples individually into the remaining wells of the plate. Preferably, each sample is loaded into two or three wells in order to provide replicate assays for each sample. Thus, 36 (in duplicate) or 24 (in triplicate) samples can be assessed per plate.

5) Cover each well with a MicroAmp™ Optical Cap (PE Biosystems part number N801-0935).

6) Insert the plates into an ABIPrism™ 7700 Sequence Detector apparatus. Adjust the settings of the apparatus to select single reporter (FAM), real-time detection.

7) Perform a PCR using the following cycling conditions:
   a) 50° C. for 2 minutes.
   b) 95° C. for 10 minutes.
   c) 40 cycles of 95° C. for 30 seconds and 62° C. for 1 minute. (Total run time: 2 hours 6 minutes)

8) Save the data and adjust the setting of the apparatus to select "Allelic Discrimination." Select VIC and FAM reporters and TAMRA quencher. Collect data from the plate containing amplified reaction mixtures.

9) Analyze the data using the "Allelic Discrimination" setting of the apparatus. It can be advisable to repeat this protocol for any sample wherein DNA in replicate wells does not clearly fall into one of the three allelic groups (AA, AG, GG) or wherein DNA in at least one well is not amplified.

The disclosures of every patent, patent application, and publication cited herein are incorporated herein by reference.

While this invention has been disclosed with reference to specific embodiments, other embodiments and variations of this invention can be devised by others skilled in the art without departing from the true spirit and scope of the invention. The appended claims include all such embodiments and equivalent variations.

What is claimed is:

1. A method of assessing the relative susceptibility of a mammal to an epithelial cancer, the method comprising determining whether the mammal comprises an A-allele of the odc gene, whereby if the mammal comprises the A-allele, then the mammal has a greater susceptibility to the epithelial cancer than a mammal of the same type which does not comprise the A-allele.

2. The method of claim 1, wherein the mammal is a human.

3. The method of claim 1, wherein the epithelial cancer is selected from the group consisting of a skin cancer, a cancer of the digestive system, an esophageal cancer, a gastric cancers, a colon cancer, a prostate cancer, a breast cancer, an hematopoietic cancer, a lung cancer, a melanoma, and a cervical cancer.

4. The method of claim 3, wherein the skin cancer is squamous cell carcinoma.

5. The method of claim 1, wherein determining whether the mammal comprises an A-allele of the odc gene comprises amplifying a reference portion of the mammal's genome.

6. The method of claim 5, wherein the reference portion is amplified using a pair of primers having nucleotide sequences SEQ ID NO: 3 and SEQ ID NO: 4.

7. The method of claim 6, wherein the reference portion is further amplified using a pair of nested primers having nucleotide sequences SEQ ID NO: 5 and SEQ ID NO: 6.

8. The method of claim 5, wherein the reference portion comprises a region of the odc gene.

9. The method of claim 5, wherein the reference portion comprises nucleotide residues +282 to +340 relative to the transcription start site.

10. The method of claim 5, wherein the reference portion has a nucleotide sequence selected from the group consisting of SEQ ID NO: 1 and SEQ ID NO: 2.

11. The method of claim 8, wherein the region comprises intron 1 of the odc gene.

12. The method of claim 8, wherein the region comprises the nucleotide residue located at position +321 relative to the transcription start site.

13. The method of claim 5, further comprising annealing an oligonucleotide probe with a target portion of the mammal's genome prior to amplifying the reference portion, wherein the target portion includes the nucleotide residue located at position +321 relative to the transcription start site of the odc gene.

14. The method of claim 13, wherein the probe comprises a fluorescent label.

15. The method of claim 14, wherein the fluorescent label is selected from the group consisting of FAM, TET, rhodamine, VIC, JOE, and HEX.

16. The method of claim 14, wherein the probe further comprises a fluorescence quencher.

17. The method of claim 16, wherein the quencher is selected from the group consisting of TAMRA and DABCYL.

18. The method of claim 17, wherein the probe has the nucleotide sequence SEQ ID NO: 14.

19. The method of claim 16, wherein one of the label and the quencher is attached to the probe within 10 nucleotide residues of the 3'-end of the probe and the other of the label and the quencher is attached to the probe within 10 nucleotide residues of the 5'-end of the probe.

20. The method of claim 16, wherein the reference portion is amplified using a DNA polymerase having 5'→3' exonuclease activity.

21. The method of claim 20, wherein the DNA polymerase is *Thermus aquaticus* DNA polymerase.

22. The method of claim 20, wherein the probe has a length from 15 to about 30 nucleotide residues.

23. The method of claim 22, wherein the size of the reference portion is not more than about 100 nucleotide residues.

24. The method of claim 1, wherein determining whether the mammal comprises an A-allele of the odc gene comprises contacting a polynucleotide derived from the mammal's genome with a molecular beacon probe, the probe having a targeting portion which is complementary to a target region of the odc gene, wherein the target region includes the nucleotide residue located at position +321 relative to the transcription start site of the odc gene.

25. The method of claim 24, wherein the targeting portion is completely complementary to the target region of the A-allele of the odc gene and has a length from about 20 to about 40 nucleotide residues.

26. The method of claim 25, further comprising contacting the polynucleotide with a second molecular beacon probe, the second probe having a targeting portion which is completely complementary to the target region of the G-allele and having a length from about 20 to about 40 nucleotide residues.

27. The method of claim 26, wherein the targeting portion of the first probe has the nucleotide sequence SEQ ID NO: 14 and the targeting portion of the second probe has the nucleotide sequence SEQ ID NO: 15.

28. The method of claim 24, wherein the target region comprises about 20 to about 30 consecutive nucleotide residues of a polynucleotide having a sequence selected from the group consisting of SEQ ID NOs: 1 and 2.

29. The method of claim 25, wherein the polynucleotide is selected from the group consisting of a chromosome of the mammal, a chromosomal fragment of the mammal, and an amplified portion of the genome of the mammal.

* * * * *

SEQUENCE LISTING

<160> NUMBER OF SEQ ID NOS: 15

<210> SEQ ID NO 1
<211> LENGTH: 59
<212> TYPE: DNA
<213> ORGANISM: Homo sapiens

<400> SEQUENCE: 1
gggccccggg cacgtgtgcg gcgcgcctcg ccggcctgca gagacacgtg gtcgccgag    59

<210> SEQ ID NO 2
<211> LENGTH: 59
<212> TYPE: DNA
<213> ORGANISM: Homo sapiens

```
<400> SEQUENCE: 2
gggccccggg cacgtgtgcg gcgcgcctcg ccggcctgcg gagacacgtg gtcgccgag        59

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: First
      pair of primers in Example 1

<400> SEQUENCE: 3
atcgtggctg gtttgagctg                                                   20

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: First
      pair of primers in Example 1

<400> SEQUENCE: 4
gtcatctgct ctgtagacac agcg                                              24

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Second
      (nested) pair of primers in Example 1

<400> SEQUENCE: 5
ggtgctataa gtagggagcg cc                                                22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Second
      (nested) pair of primers in Example 1

<400> SEQUENCE: 6
ccgaagggtt gggaaagagg                                                   20

<210> SEQ ID NO 7
<211> LENGTH: 6
<212> TYPE: DNA
<213> ORGANISM: Artificial Sequence
<220> FEATURE:
<223> OTHER INFORMATION: Description of Artificial Sequence:
      Hexanucleotide core of Myc/Max dimer binding site

<400> SEQUENCE: 7 cacgtg                                                                   6

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: A allele
      detection probe in Example 1
```

```
<400> SEQUENCE: 8
ccggcctgca gagacacgtg gtcgccgagc g                                           31

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: A allele
      detection probe in Example 1

<400> SEQUENCE: 9
ggccggacgt ctctgtgcac cagcggctcg c                                           31

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: G allele
      detection probe in Example 1

<400> SEQUENCE: 10
ccggcctgcg gagacacgtg gtcgccgagc g                                           31

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: G allele
      detection probe in Example 1

<400> SEQUENCE: 11
ggccggacgc ctctgtgcac cagcggctcg c                                           31

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Forward
      primer for allelic discrimination method of Example 2

<400> SEQUENCE: 12
cctgggcgct ctgaggt                                                           17

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Reverse
      primer for allelic discrimination method of Example 2

<400> SEQUENCE: 13
aggaagcggc gcctcaa                                                           17

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: TaqMan(TM)
      Allele A Probe in Example 2

<400> SEQUENCE: 14
```

```
cacgtgtctc tgcaggccgg                                                    20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: TaqMan(TM)
      Allele G Probe in Example 2

<400> SEQUENCE: 15
cacgtgtctc cgcaggccg                                                     19
```